United States Patent [19]

Saito et al.

[11] Patent Number: 5,191,076
[45] Date of Patent: Mar. 2, 1993

[54] ACETYLOXYLATION PROCESS FOR PRODUCING 4-ACETOXYAZETIDINONES WITH OSMIUM CATALYST

[75] Inventors: Takao Saito; Hidenori Kumobayashi; Shunichi Murahashi, all of Tokyo, Japan

[73] Assignee: Takasago International Corporation, Tokyo, Japan

[21] Appl. No.: 798,150

[22] Filed: Nov. 26, 1991

[30] Foreign Application Priority Data

Nov. 30, 1990 [JP] Japan .................................. 2-335727

[51] Int. Cl.$^5$ ..................... C07D 205/08; C07B 41/12
[52] U.S. Cl. .................................................. 540/357
[58] Field of Search ......................................... 540/357

[56] References Cited

FOREIGN PATENT DOCUMENTS 0180252 5/1986 European Pat. Off. .
0290385 11/1988 European Pat. Off. .
0371875 6/1990 European Pat. Off. .

OTHER PUBLICATIONS

Braun et al, TCS Chem Comm 1972, p. 229.
Murahashi, Tetrahedron Letters, vol. 32, No. 19, pp. 2145-2148 (1991).

*Primary Examiner*—Mark L. Berch
*Attorney, Agent, or Firm*—Sughrue, Mion, Zinn, Macpeak & Seas

[57] ABSTRACT

A process for producing a 4-acetoxyazetidinone represented by formula (I):

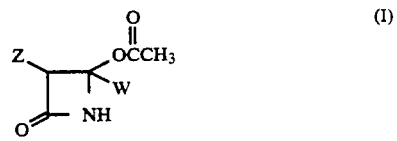

(I)

wherein Z represents a hydrogen atom, a lower alkyl group, or a protected or unprotected hydroxyethyl group; and W represents a hydrogen atom, a lower alkyl group, or a group of —COOR$^1$, wherein R$^1$ represents a lower alkyl group, is disclosed, which comprises reacting an azetidinone represented by formula (II):

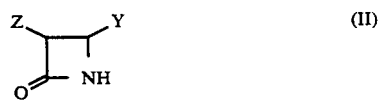

(II)

wherein Z is as defined above; and Y represents a hydrogen atom, carboxyl group, a lower alkyl group, or a group of —COOR$^1$, wherein R$^1$ represents a lower alkyl group, with acetic acid and an oxidizing agent in the presence of, as a catalyst, an anhydrous or hydrous osmium compound represented by OsX$_3$, wherein X represents a chlorine atom, a bromine atom, or an iodine atom.

8 Claims, No Drawings

ACETYLOXYLATION PROCESS FOR PRODUCING 4-ACETOXYAZETIDINONES WITH OSMIUM CATALYST

FIELD OF THE INVENTION

The present invention relates to a process for producing an intermediate useful for synthesis of penem antibiotics represented by thienamycin. More particularly, the present invention relates to a process for producing a 4-acetoxyazetidinone derivative represented by formula (I):

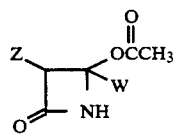

wherein Z represents a hydrogen atom, a lower alkyl group, or a protected or unprotected hydroxyethyl group; and W represents a hydrogen atom, a lower alkyl group, or a group of —COOR$^1$, wherein R$^1$ represents a lower alkyl group.

BACKGROUND OF THE INVENTION

Since penem antibiotics represented by thienamycin have a broad antibacterial spectrum, they are being watched with keen interest as medicines.

Various processes for producing penem antibiotics have been proposed in, for example, Kametani, *Heterocycles*, 17, pp. 463–506 (1982) and Shibuya, *Yuki Gosei Kauaku*, 41, p. 62 (1983). Of these, the processes in which the desired antibiotics are synthesized via 4-acetoxyazetidinone derivatives represented by formula (I) as intermediates are advantageous in that various penem antibiotics can be produced because compounds (I) can react with a variety of nucleophilic agents.

Conventionally known methods for producing 4-acetoxy-azetidinone derivatives (I) include oxidation of a 4-carboxy-azetidinone with lead tetraacetate [*Tetrahedron Letters*, 23, p. 2293 (1982)], electrolytic oxidation of a 4-carboxyazetidinone [*Tetrahedron Letters*, 29, p. 1409 (1988)], oxidation of a 4-acetylazetidinone with m-chloroperbenzoic acid (JP-A-61-50964) (the term "JP-A" as used herein means an "unexamined published Japanese patent application"}, and treatment of a 4-silyloxy-azetidinone derivative with acetic anhydride (European Patent 247,378).

In the above methods, in order to introduce an acetoxy group at the 4-position of the azetidinone, an azetidinone derivative having a specific substituent group at the 4-position thereof should first be synthesized, and an acetoxy group should be then introduced by converting this substituent group. However, these methods are defective in that not only the production of such an azetidinone derivative having a specific substituent group at the 4-position thereof is troublesome, but the conversion of the substituent group at the 4-position into an acetoxy group is difficult. For these reasons, the above methods have been unavoidably disadvantageous as an industrial method.

As an expedient for eliminating the above-described drawbacks, it has been proposed to introduce an acetoxy group into an azetidinone at the 4-position thereof by use of a ruthenium compound (JP-A-2-231471). However, in industrialization of this method, further improvements in catalytic activity have been desired.

SUMMARY OF THE INVENTION

Under these circumstances, the present inventors have made intensive studies. As a result, it has now been found that by reacting an azetidinone with acetic acid and an oxidizing agent in the presence of an osmium compound as a catalyst, an acetoxy group can be easily introduced into the azetidinone at the 4-position thereof and the catalytic activity is higher than that in a method employing a ruthenium compound as a catalyst. The present invention has been completed based on this finding.

Accordingly, an object of the present invention is to provide a process for producing a 4-acetoxyazetidinone represented by formula (I):

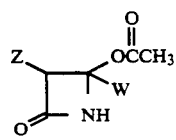

wherein Z represents a hydrogen atom, a lower alkyl group, or a protected or unprotected hydroxyethyl group; and W represents a hydrogen atom, a lower alkyl group, or a group of —COOR$^1$, wherein R$^1$ represents a lower alkyl group, which comprises reacting an azetidinone represented by formula (II):

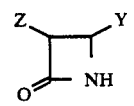

wherein Z is as defined above; and Y represents a hydrogen atom, carboxyl group, a lower alkyl group, or a group of —COOR$^1$, wherein R represents a lower alkyl group, with acetic acid and an oxidizing agent in the presence of, as a catalyst, an anhydrous or hydrous osmium compound represented by OsX$_3$, wherein X represents a chlorine atom, a bromine atom, or an iodine atom.

DETAILED DESCRIPTION OF THE INVENTION

The alkyl moiety in the lower alkyl group or lower alkoxy group as referred to in the present invention preferably has from 1 to 4 carbon atoms.

Examples of the azetidinone (II) which is used as a raw material in the present invention include azetidin-2-one, 3-methylazetidin-2-one, 3-ethylazetidin-2-one, 3-hydroxyethylazetidin-2-one, 3-methyl-4-carboxyazetidin-2-one, 3-ethyl-4-carboxyazetidin-2-one, 3-(protected) hydroxyethyl-4-carboxyazetidin-2-one, 4-methylazetidin2-one, and 4-methoxycarbonylazetidin-2-one.

As the protective group of the hydroxyl group, those which are generally used for protection of hydroxyl group in lactam compounds can be used. Examples thereof include silyl groups (e.g., trimethylsilyl, triethylsilyl, tert-butyldi-methylsilyl, and diphenyl-tert-butylsilyl), a benzyloxycarbonyl group, a p-nitrobenzyloxycarbonyl group, and an o-nitrobenzyl-oxycarbonyl group.

Of the above-enumerated azetidinone derivatives (II), a compound in which Z is a (protected) hydroxyethyl group, and Y is hydrogen atom can be produced from a compound of formula (III) which is derived, for example, from acetoacetic acid Ber., 92, p. 1599 (1959)], according to the following reaction scheme.

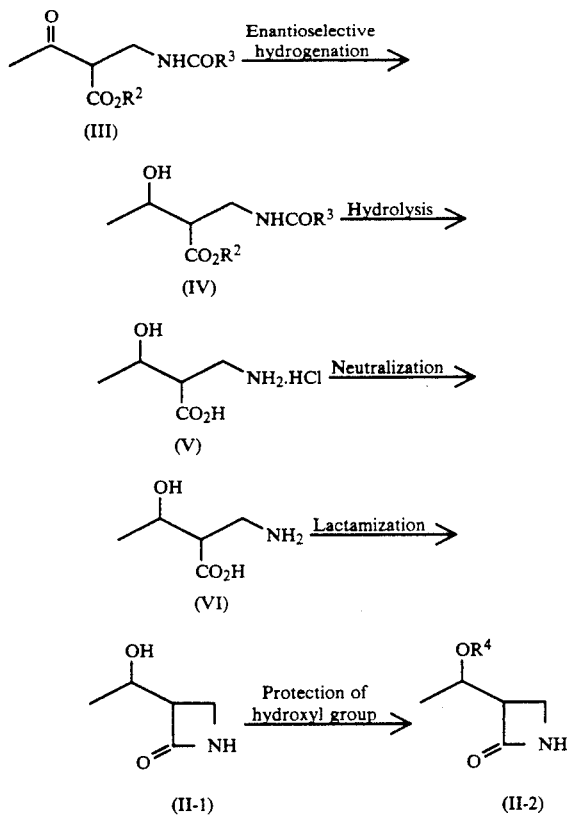

In the above reaction scheme, $R^2$ represents a protective group of a carboxylic acid; $R^3$ represents a hydrogen atom, a lower alkyl group, a lower alkoxy group, or a phenyl or benzyloxy group which may be substituted with a lower alkyl group or a lower alkoxy group; and $R^4$ represents a protective group of a hydroxyl group.

That is, compound (III) is subjected to enantio-selective hydrogenation using a ruthenium-optically active phosphine complex as a catalyst to give compound (IV), which is then hydrolyzed with a dilute acid, etc. into compound (V). Compound (V) is neutralized to give compound (VI), which is then lactamization to obtain compound (II-1). Subsequently, the hydroxyl group of this compound (II-1) is protected to give compound (II-2).

Examples of the osmium compound used as a catalyst in the present invention are anhydrous or hydrous osmium tri-chloride, osmium tribromide, and osmium triiodide. Of these, osmium trichloride is particularly preferred.

The oxidizing agent used in the present invention is not especially limited. Examples thereof include peroxides of various carboxylic acids, other peroxides, high-concentration bleaching powder, ozone, cyclohexene ozonide, sodium peroxide, sodium perborate, iodosylbenzene diacetate, iodosylbenzene, sodium metaperiodate, and sodium paraperiodate. Specific examples of the carboxylic acid peroxides include peracetic acid, perpropionic acid, and m-chloroperbenzoic acid. These compounds may be ones which are commercially available, or they may be prepared separately from a carboxylic acid and hydrogen peroxide before the reaction. Further, specific examples of other peroxides include methyl ethyl ketone peroxide, methyl isobutyl ketone peroxide, cyclohexanone peroxide, methyl-cyclohexanone peroxide, diacetyl peroxide, dipropionyl peroxide, and diisobutyryl peroxide. Use of peracetic acid as the oxidizing agent is advantageous in that it is not particularly required to add acetic acid to the reaction system because acetic acid is usually incorporated in peracetic acid.

It is preferred in the present invention to conduct the reaction with acetic acid in the presence of an acetic acid salt, since the presence of an acetic acid salt results in an improved yield. Examples of the acetic acid salt include sodium acetate, potassium acetate, and lithium acetate.

The present invention can, for example, be practiced as follows. Compound (II), an oxidizing agent, acetic acid, and an osmium compound are dissolved or suspended in a suitable solvent, and the solution or suspension is reacted with stirring at a temperature of $-10°$ C. to $50°$ C. for from 10 minutes to 5 hours, and preferably about 2 hours. The addition order and method of the raw material compound, catalyst, and other ingredients are not particularly limited. It is, however, desirable that the oxidizing agent be added gradually after all the other ingredients.

As the solvent, organic solvents such as acetonitrile, methylene chloride, acetone, acetic acid, and acetic acid esters can be used. The amount of acetic acid used is preferably from 10 to 60 mole, and more preferably from 20 to 40 mole, per mole of compound (II), while the amount of the oxidizing agent used is preferably from 1 to 8 mole, and more preferably from 2 to 3 mole, per mole of compound (II). The amount of the osmium compound which is used as a catalyst is preferably from 0.001 to 0.05 mole, and more preferably from 0.01 to 0.03 mole, per mole of compound (II).

Isolation of the desired compound from the resulting reaction mixture can be accomplished by a known means such as, for example, recrystallization and column chromatography.

The process of the present invention is more advantageous in efficiently obtaining a 4-acetoxyazetidinone derivative than the above-described method employing a ruthenium compound as a catalyst. That is, in the conventional method employing a ruthenium compound as a catalyst, the ruthenium compound should be used in an amount as large as about 10 mole % of the substrate azetidinone, whereas in the present invention, a 4-acetoxyazetidinone can be obtained in good yield as long as the osmium compound is used even in an amount as small as about 2 mole % of the substrate.

The compounds obtained by the process of the present invention are industrially useful compounds. Of these, (1',R,3R,4R)-4-acetoxy-3-(1'-tert-butyldimethylsilyloxy)-ethylazetidin-2-one of the formula:

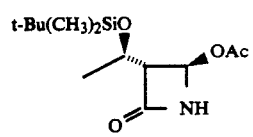

wherein t-Bu is a tert-butyl group; and Ac is an acetyl group, is a particularly useful intermediate indispensable for syntheses of thienamycin and other important penem antibiotics. According to the present invention, this compound can be obtained at a diastereomer selectivity of 99% or more.

As described above, the process of the present invention can produce 4-acetoxyazetidinone derivatives (I) useful as intermediates for synthesis of penem antibiotics by simple procedures with good catalytic activity and, hence, is an industrially advantageous process.

The present invention will be explained below in more detail with reference to the following examples, which should not be construed to be limiting the scope of the invention.

EXAMPLE 1

Synthesis of 4-Acetoxyazetidin-2-one

To a mixture of 200 mg (2.8 mmole) of azetidin-2-one, 230 mg (2.8 mmole) of anhydrous sodium acetate, 2 ml of acetic acid, and 17 mg (2 mole % based on the amount of azetidin-2-one) of osmium trichloride trihydrate was added dropwise, with stirring, 1.56 g (6.2 mmole) of a 30% peracetic acid solution in ethyl acetate at room temperature over a period of 2 hours or more. The reaction mixture was poured into 50 ml of water and extracted with n-hexane. The extract was separated and purified by silica gel column chromatography (n-hexane/ethyl acetate=1/1 by volume). Thus, 280 mg (2.2 mmole, percent yield: 78%) of 4-acetoxyazetidin-2-one in a colorless oily state was obtained.

EXAMPLES 2 TO 6

The same procedures as in Example 1 were repeated except that the substrate azetidinone and the amount (mole %) of osmium trichloride trihydrate relative to the amount of the substrate were changed as shown in Table 1. As a result, the 4-acetoxyazetidinones as shown in Table 1 were obtained from the respective substrates in respective percent yields shown in the same table.

TABLE 1

| Ex. No. | Substrate | Synthesized 4-Acetoxyazetidinone | $OsCl_3 \cdot 3H_2O$ (mol %) | Percent Yield (%) |
|---|---|---|---|---|
| 2 | 3-ethyl-azetidin-2-one (CH$_3$ substituent) | 4-OAc-3-ethyl-azetidin-2-one | 2 | 76 |
| 3 | 3-(1-hydroxyethyl)-azetidin-2-one (HO) | 4-OAc-3-(1-hydroxyethyl)-azetidin-2-one (two diastereomers, 8:2) | 2 | 43 |
| 4 | 3-[1-(t-Bu(CH$_3$)$_2$SiO)ethyl]-azetidin-2-one | 4-OAc-3-[1-(t-Bu(CH$_3$)$_2$SiO)ethyl]-azetidin-2-one | 2 | 92 |
| 5 | 3-(CO$_2$H-methyl)-azetidin-2-one | 4-OAc-3-(CO$_2$H-methyl)-azetidin-2-one | 2 | 77 |
| 6 | 3-(CO$_2$CH$_3$-methyl)-azetidin-2-one | 4-OAc-3-(CO$_2$CH$_3$-methyl)-azetidin-2-one | 2 | 48 |

EXAMPLES 7 TO 11

Synthesis of (1'R,3R,4R)-4-Acetoxy-3-(1'-tert-butyldimethylsilyloxy)ethylazetidin-2-one To a mixture of 200 mg (0.87 mmole) of (1'R,3S)-3-(1'-tert-butyldimethylsilyloxy)ethylazetidin-2one, 72 mg (0.87 mmole) of anhydrous sodium acetate, 2 ml of acetic acid, and 7 mg of osmium trichloride trihydrate was added dropwise, with stirring, 1.91 mmole of each of the oxidizing agents as shown in Table 2 at room temperature over a period of 2 hours or more. (The oxidizing agents were used as they were or in the form of a methylene chloride solution.) Each of the reaction mixtures was poured into 50 ml of water and extracted with n-hexane. The extract was distilled in vacuo and separated and purified by silica gel column chromatography (n-hexane/ethyl acetate=8/1 by volume). Thus, (1'R,3R,4R)-4-acetoxy-3-(1'-tert-butyldimethylsilyloxy)ethylazetidin-2-one was obtained in a percent yield shown in Table 2.

TABLE 2

| Example No. | Oxidizing Agent | $OsCl_3 \cdot 3H_2O$ (mole %) | Percent Yield (%) |
|---|---|---|---|
| 7 | CH$_3$CO$_3$H | 2.3 | 92 |
| 8 | mCPBA[1] | 2.3 | 73 |
| 9 | PhI(OAc)$_2$[2] | 2.3 | 70 |
| 10 | PhIO[3] | 2.3 | 67 |
| 11 | MEKP[4] | 2.3 | 70 |

[1]: m-chloroperbenzoic acid
[2]: iodosylbenzene diacetate
[3]: iodosylbenzene
[4]: methyl ethyl ketone peroxide

EXAMPLE 12

Synthesis of 4-Acetoxy-3-ethylazetidin-2-one

To a solution prepared by mixing 500 mg (5 mmole) of 3-ethylazetidin-2-one, 415 mg (5 mmole) of anhydrous sodium acetate, 5 ml of acetic acid, and 30 mg (abut 2 mole % based on the amount of 3-ethylazetidin-2-one) of osmium trichloride trihydrate was added dropwise, with stirring , 2.8 g (11 mmole) of a 30% peracetic acid solution in ethyl acetate at room temperature over a period of 2 hours or more. The reaction mixture was further stirred at room temperature for 4 hours, subsequently poured into 80 ml of water, and then extracted thrice with 100 ml of hexane. The extract was dried over anhydrous magnesium sulfate, and the solvent was removed by evaporation under reduced pressure. The residue was separated and purified by silica gel column chromatography (n-hexane/ethyl acetate=1/1 by volume). Thus, 780 mg of 4-acetoxy-3-ethylazetidin-2-one was obtained. The percent yield was 78%.

$^1$H-NMR (CDCl$_3$) δ ppm: 0.99 (3H, t, J=7.4 Hz), 1.75 (2H, m), 2.10 (3H, s), 3.08 (1H, m), 5.78 (1H, d, J=1.25 Hz), 6.55 (1H, b, NH)

While the invention has been described in detail and with reference to specific embodiments thereof, it will be apparent to one skilled in the art that various changes and modifications can be made therein without departing from the spirit and scope thereof.

What is claimed is:

1. A process for producing a 4-acetoxyazetidinone represented by formula (I):

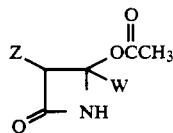

(I)

wherein Z represents a hydrogen atom, a lower alkyl group, or a protected or unprotected hydroxyethyl group; and W represents a hydrogen atom, a lower alkyl group, or a group of the formula —COOR$^1$, wherein R$^1$ represents a lower alkyl group, which comprises reacting an azetidinone represented by the formula (II):

(II)

wherein Z is as defined above; and Y represents a hydrogen atom, a carboxyl group, a lower alkyl group, or a group of the formula —COOR$^1$, wherein R$^1$ represents a lower alkyl group, with acetic acid and an oxidizing agent in the presence of, as a catalyst, an anhydrous or hydrous osmium compound represented by the formula OsX$_3$ or hydrated versions thereof, wherein X represents a chlorine atom, a bromine atom, or an iodine atom, with the proviso that when Y represents a hydrogen atom, a lower alkyl group, or —COOR$^1$, then W represents Y, and when Y represents —COOH, then W represents a hydrogen atom.

2. A process as in claim 1, wherein said oxidizing agent is peracetic acid.

3. A process as in claim 1, wherein said osmium compound is osmium trichloride.

4. A process as in claim 1, wherein the reaction is carried out with at a temperature of from −10° C. to 50° C. for from 10 minutes to 5 hours.

5. A process as in claim 1, wherein acetic acid is used in an amount of from 10 to 60 mole per mole of said azetidinone represented by formula (II).

6. A process as in claim 1, wherein said oxidizing agent is used in an amount of from 1 to 8 mole per mole of said azetidinone represented by formula (II).

7. A process as in claim 1, wherein said osmium compound is used in an amount of from 0.001 to 0.05 mole per mole of said azetidinone represented by formula (II).

8. A process as in claim 1, wherein the reaction is carried out in the further presence of an acetic acid salt.

* * * * *